United States Patent [19]

Gaull

[11] Patent Number: 4,545,977

[45] Date of Patent: Oct. 8, 1985

[54] COMPOSITIONS AND METHODS FOR TREATING SEVERE ACNE WITH ISOTRETINOIN

[75] Inventor: Gerald E. Gaull, New York, N.Y.

[73] Assignee: G. D. Searle & Co., Skokie, Ill.

[21] Appl. No.: 690,707

[22] Filed: Jan. 11, 1985

[51] Int. Cl.[4] .................................................. A61K 31/20
[52] U.S. Cl. ........................................ 424/10; 514/559; 514/578; 514/725; 514/859; 514/922
[58] Field of Search .................. 424/10; 514/559, 578, 514/859, 922, 725

[56] References Cited

FOREIGN PATENT DOCUMENTS 1335867  10/1973  United Kingdom .

OTHER PUBLICATIONS

Merck Index, 9th ed., p. 1175, paragraph 8850, 1976.

*Primary Examiner*—Leonard Schenkman
*Attorney, Agent, or Firm*—John J. McDonnell

[57] ABSTRACT

A therapeutically effective amount of isotretinoin is co-administered to patients suffering from severe cystic acne with a protective amount of taurine which reduces the side effects of isotretinoin.

13 Claims, No Drawings

COMPOSITIONS AND METHODS FOR TREATING SEVERE ACNE WITH ISOTRETINOIN

BACKGROUND OF THE INVENTION

This invention relates to the treatment of acne and more particularly relates to improved compositions and methods for treating severe cystic acne with isotretinoin or a related retinoid wherein taurine is co-administered with the retinoid to reduce the side effects thereof.

Isotretinoin (13-cis-retinoic acid) is sold by Roche Laboratories under the trademark ACCUTANE ®. The compound, which is related to both retinoic acid and retinol (Vitamin A), is considered to be a significant advance in the treatment of patients suffering from severe cystic acne. Isotretinoin and related retinoids or retinoic acid derivatives inhibit sebaceous gland function and keratinization and are considered to combat virtually all mechanisms that create acne.

Unfortunately, in view of the significant adverse side effects associated with its use, isotretinoin therapy is reserved for patients with severe cystic acne who are unresponsive to conventional therapy, including systemic antibiotics. Of particular concern is the teratogenicity of the drug which is considered to produce such common patterns of malformations in infants as to be referred to as the Accutane Syndrome. In view of the teratogenicity of the retinoids, including isotretinoin, patients who are pregnant or are not using an effective contraceptive, should not be treated with this class of acne agents. A substantial problem exists when dealing with teen-age girls or single women who may deny they are sexually active, as physicians are reluctant to disbelieve their patients.

In view of the value of isotretinoin therapy, there exists a substantial need for compositions and methods that reduce the side effects of this retinoid without decreasing its effectiveness in the treatment of severe cystic acne. Reduction of side effects might also enable the agent to be more widely used. The present invention fulfills that need.

SUMMARY OF THE INVENTION

In the practice of the present invention, a therapeutically effective amount of isotretinoin, or another retinoic acid derivative which is effective in the treatment of cystic acne, is administered in conjunction with a protective amount of taurine which provides protection against the side effects of the retinoic acid derivatives. It is preferred to co-administer the retinoid and taurine in a unitary dosage form, i.e., a capsule or tablet containing both agents.

The term "protective amount", as used herein, refers to the effective dosage of taurine which affords substantial reduction of the side effects of isotretinoin or other retinoid being administered to a patient suffering from severe cystic acne. Generally speaking, oral dosages of from 1 to 100 mg/kg daily are considered to be a protective dose.

A therapeutically effective dosage of isotretinoin is from 1 to 2 mg/kg of body weight daily, preferably administered orally in two divided doses.

Taurine (2-aminoethanesulfonic acid) is present in bile combined with cholic acid and also occurs in the lungs and flesh extract of oxen, in mussels, oysters, and shark blood. The material may be isolated from ox bile by the method of Hammarsten, *Z Physiol. Chem.* 32, 456 (1901) or from the large muscle of abalone as reported by Schmidt et al., *J. Biol. Chem.* 33, 499 (1918). Taurine may also be prepared by the method described by Marvel et al., *Org. Syn.* 10, 98(1930) or Schick et al., *Ind. Eng. Chem.* 39, 906 (1940).

DETAILED DESCRIPTION OF PREFERRED EMBODIMENTS

In the practice of the present invention, a therapeutically effective dose of isotretinoin, or another therapeutically effective retinoid which exhibits similar side effects, is co-administered to a patient in need of such treatment with a protective amount of taurine.

Isotretinoin is generally administered to patients suffering from severe cystic acne in oral dosages of from 1 to 2 mg/kg of body weight daily, in two divided daily dosages, for fifteen to twenty weeks. Taurine is co-administered in oral dosages of from 1 to 100 mg/kg daily, preferably in two divided dosages taken with the retinoic acid derivative.

While taurine can be separately administered, it is preferred to administer both the retinoic acid derivative and the protective agent in a unitary dosage form to insure that the protection of human cells against damage from the retinoid is obtained. This is particularly critical when the drug is administered to women of child-bearing years to provide protection against birth defects in the event pregnancy occurs during isotretinoin therapy.

In cases where the acne patient is a woman of child-bearing years, it may be desirable to initiate taurine therapy for six to eight weeks prior to the co-administration of taurine and a retinoic acid derivative such as isotretinoin and to continue taurine administration for a period of four to eight weeks after stopping isotretinoin administration.

Generally speaking the preferred compositions of the present invention comprise capsules or tablets containing from 10 to 40 mg of isotretinoin and from 10 to 4000 mg of taurine per unit dosage. The oral dosage forms may additionally comprise pharmaceutically acceptable diluents, binders, disintegrants, flavoring agents, lubricants, and other suitable excipients which are standard in the art.

In the case of compressed tablets, suitable diluents include dicalcium phosphate, calcium sulfate, lactose, mannitol, starch, sorbitol, sucrose, and the like. Suitable binders include, but are not limited to, starches such as corn starch, methylcellulose, ethylcellulose, lactose, and the like. Suitable lubricants include, but are not limited to, talc, magnesium stearate, calcium stearate, stearic acid, and hydrogenated vegetable oils. Suitable tabletting disintegrants include starches, clays, celluloses and algins or gums, i.e. corn starch, potato starch, methyl cellulose, agar, betonite, carboxymethylcellulose, alginic acid, guar gum and the like.

Suitable diluents for inclusion in filled capsules include, but are not limited to lactose, mannitol, calcium carbonate and magnesium carbonate.

The invention claimed is:

1. A pharmaceutical composition for the treatment of severe cystic acne comprising a therapeutically effective amount of isotretinoin and a protective amount of taurine.

2. The pharmaceutical composition of claim 1 wherein said composition is in oral unit dosage form.

3. The pharmaceutical composition of claim 1 wherein said composition comprises from 10 to 40 mg per unit dose of isotretinoin and from 10 to 4000 per unit dose of taurine.

4. The pharmaceutical composition of claim 2 wherein said oral unit dosage form is a filled capsule.

5. The pharmaceutical composition of claim 3 wherein said oral unit dosage form is a tablet.

6. The pharmaceutical composition of claim 2 wherein said oral unit dosage from is a filled capsule.

7. The pharmaceutical composition of claim 3 wherein said oral unit dosage form is a filled capsule.

8. An improved method of treating severe cystic acne comprising co-administering to a patient in need of such treatment a therapeutically effective amount of isotretinoin and a protective amount of taurine.

9. The method of claim 8 wherein isotretinoin is administered is dosages of from 1 to 2 mg/kg of body weight daily.

10. The method of claim 8 wherein taurine is administered in dosages of from 1 to 100 mg/kg of body weight daily.

11. The method of claim 9 wherein taurine is administered in dosages of from 1 to 100 mg/kg of body weight daily.

12. The method of claim 8 wherein taurine is additionally administered for a period of 4 to 8 weeks after isotretinoin therapy has been stopped.

13. The method of claim 8 wherein taurine is additionally administered for a period of 4 to 8 weeks prior to initiation of isotretinoin administration.

* * * * *